United States Patent [19]

Combourieu et al.

[11] 4,409,221
[45] Oct. 11, 1983

[54] 1,2,3,4,4A,9B-HEXAHYDRO-4A-PIPERAZINYLMETHYL-4-DIBENZOFURANONE OR -DIBENZOFURANOL DERIVATIVES

[75] Inventors: Michel Combourieu; Jean-Claude Laigle, both of Aurillac; Norbert Busch, Manzat, all of France

[73] Assignee: Riom Laboratories - Cerm S.A., Riom, France

[21] Appl. No.: 386,621

[22] Filed: Jun. 9, 1982

[30] Foreign Application Priority Data

Jun. 12, 1981 [FR] France ................................ 81 11672

[51] Int. Cl.³ .................. A61K 31/495; C07D 405/00; C07D 405/06; C07D 307/81
[52] U.S. Cl. ...................................... 424/250; 544/360; 544/375; 549/460; 549/461
[58] Field of Search ................. 544/360, 375; 424/250

[56] References Cited

U.S. PATENT DOCUMENTS 3,317,527 5/1967 Skaletzky ............................ 544/375
3,337,563 8/1967 Skaletzky ............................ 544/375
3,496,181 2/1970 Skaletzky ............................ 544/375

Primary Examiner—Donald G. Daus
Assistant Examiner—S. A. Gibson
Attorney, Agent, or Firm—Abelman, Frayne & Rezac

[57] ABSTRACT

The present invention is dealing with compounds of the formula:

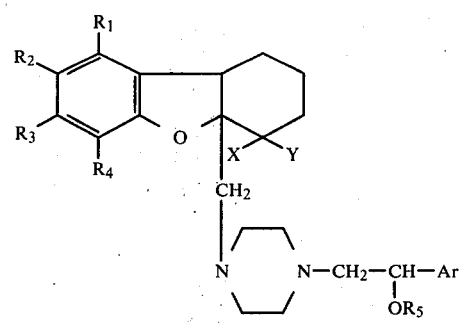

and pharmaceutically acceptable salts thereof, in which $R_1$, $R_2$, $R_3$ and $R_4$ are identical or different and represent hydrogen, halogen, lower alkyl or alkoxy or trifluoromethyl; $R_5$ represents hydrogen or lower alkyl, X represents hydrogen and Y represents hydroxy, or X and Y together represent oxygen and Ar represents an optionally substituted aromatic moiety, having potent anti-bronchoconstrictor properties.

8 Claims, No Drawings

1,2,3,4,4A,9B-HEXAHYDRO-4A-PIPERAZINYL-METHYL-4-DIBENZOFURANONE OR -DIBENZOFURANOL DERIVATIVES

The present invention relates to 1,2,3,4,4a,9b-hexahydro-4a-piperazinylmethyl-4-dibenzofuranone or -dibenzofuranol derivatives, processes for their synthesis and pharmaceutical preparations containing same.

More particularly the invention relates to compounds represented by the following general formula I:

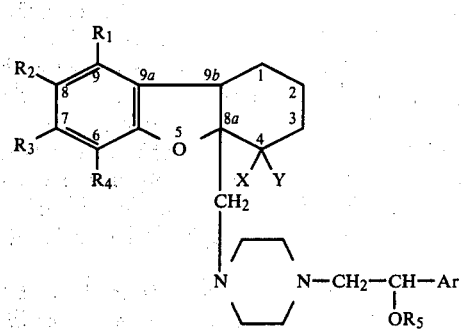

and pharmaceutically acceptable salts thereof, in which $R_1$, $R_2$, $R_3$ and $R_4$ are identical or different and represent hydrogen, halogen, lower alkyl or alkoxy or trifluoromethyl; $R_5$ represents hydrogen or lower alkyl, X represents hydrogen and Y represents hydroxy, or X and Y together represent oxygen and Ar represents an optionally substituted aromatic moiety.

A lower alkyl radical used in the definitions of $R_1$–$R_4$ and $R_5$ denotes a linear or branched alkyl radical having from 1 to 6 carbon atoms and preferably from 1 to 4 carbon atoms, such as methyl, ethyl, propyl, n.butyl, sec. butyl and tert.butyl. The alkyl moiety of the alkoxy radical has a similar meaning.

Halogen means fluorine, chlorine, bromine or iodine, whereby fluorine and chlorine are to be preferred.

The aromatic moiety as meant in the definition of Ar is preferably phenyl or pyridyl, optionally substituted by alkyl (1–4 C), alkoxy (1–4 C) or halogen. More preferred aromatic moieties are: phenyl, alkyl substituted phenyl, 3-pyridyl and 4-methyl-3-pyridyl.

Numerous publications have been made on hexahydrodibenzofurans, but the substitutions envisaged in these known molecules, do not correspond in any case to the particular substitutions in the present compounds according to the invention.

As closest prior art U.S. Pat. No. 3,496,181 may be cited. This patent discloses 1,2,3,4,4a,9b-hexahydro-4a-(4-methyl-1-piperazinyl)-8-dibenzofuranol as an intermediate in the synthesis of compounds having pseudo-cholinesterase inhibiting properties.

The compounds of formula I may be prepared by methods in actual use or described in the literature. For example the compounds of formula I can be prepared by condensation of a compound of the formula II:

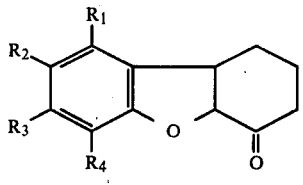

in which $R_1$, $R_2$, $R_3$ and $R_4$ have the meanings assigned above, with a compound of the formula III:

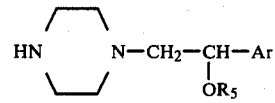

in which $R_5$ and Ar have the meanings assigned above, in the presence of formaldehyde or paraformaldehyde. This condensation, which is known as the Mannich reaction, is preferably carried out in absolute ethanol, in the presence of hydrochloric acid and with an excess of paraformaldehyde.

The condensation reaction results in a compound of formula I, in which X and Y together represent oxygen.

To obtain the compounds of formula I, in which X represents hydrogen and Y hydroxy, a reduction is carried out in addition to the above Mannich reaction, for example, by means of a complex metal hydride, such as sodiumborohydride.

The 1,2,3,4,4a,9b-hexahydro-4-dibenzofuranones of formula II used as starting materials, may be prepared, for example, by treating a 2-(2-cyclohexenyl)phenol with an organic peracid, so as to yield the corresponding 1,2,3,4,4a,9b-hexahydro-4-benzofuranol, the hydroxy function of which is then oxydised, for example, by means of pyridinium chlorochromate.

Pharmaceutically acceptable salts of the compounds I are obtained by reacting a compound I with a suitable organic or inorganic acid such as HCl, HBr, phosphoric acid, acetic acid, maleic acid, fumaric acid, tartaric acid, citric acid, etc.

The compounds of formula I contain chiral centra, so that some stereo-isomers of formula I are possible. These stereo-isomers (either in the form of a racemate or in the form of separate enantiomers) also belong to the compounds of the invention. Said stereo-isomers can be separated from the mixture by conventional separation and/or resolution techniques.

The compounds according to the invention and their pharmaceutically acceptable salts are useful as pharmaceutically active compounds, particularly on account of their remarkable anti-bronchoconstrictor properties.

In combination with the usual pharmaceutical excipients the compounds of the invention can be administered enterally or parenterally, preferably at a daily dosage of between 0.5 and 25 mg per kg body weight. The preferred daily oral dosage in human beings is between 200 and 1,000 mg.

The anti-bronchoconstrictor activity of the compounds of the invention is evaluated in guineapigs by the KONZETT and ROSSLER technique.

After being anaesthetised with ethyl carbamate and submitted to tracheotomy, the animals are given artificial breathing at constant volume and the intertracheal pressure is recorded, which makes an indirect measurement of the total pulmonary resistance possible. Histamine (5 μg/kg$^{-1}$ i.v.) is administered before, and at different time intervals after, intravenous administration of the compounds of the invention.

The activity of the product under study is evaluated by comparing the amplitudes of the bronchospasms before and after treatment and calculating the percentage change. The duration of action of the compounds under study has also been observed. The results recorded are reported in the Table below. (Table I). This table also contains an acute toxicity rating (LD$_{50}$) determined by oral administration in mice.

TABLE I

| Compound No. [see Table II of the Examples] | Dose (in mg/kg$^{-1}$) I.V. | Percentage Inhibition | Duration (in min.) | Rating LD$_{50}$ (mg/kg$^{-1}$) |
| --- | --- | --- | --- | --- |
| 1 | 5 | 100 ± 0 | >60 | |
| | 1 | 87.7 ± 6.6 | >60 | |
| 2 | 5 | 95 ± 3.1 | >60 | 900 |
| 3 | 5 | 97.5 ± 2.5 | >45 | 320 |
| 5 | 5 | 80.2 ± 9.9 | >45 | 900 |
| 6 | 5 | 48.2 ± 9.2 | >45 | 900 |
| 8 | 1 | 95.5 ± 4.6 | >60 | 480 |

In addition, the bronchosparm experiment was repeated, but replacing histamine with serotonine, (20 μg/kg$^{-1}$, I.V.). Compound No. 1, administered intravenously at the dose of 5 mg/kg$^{-1}$, showed an inhibition of 87.6% observed during 60 minutes.

These results clearly show that the compounds of the invention strongly and durably inhibit histamine type and serotoninergic bronchospasms. The compounds I are therefore useful as antibronchoconstrictors.

The preparation of the compounds of the invention is illustrated in greater detail by reference to the following examples.

EXAMPLE 1

1,2,3,4,4a,9b-hexahydro-4a-(1-[4-(2-ethoxy-2-phenyl)ethyl]piperazinyl)methyl-4-dibenzofuranone 12 ml of concentrated hydrochloric acid, 25 g (0.133 M) of 1,2,3,4,4a,9b-hexahydro-4-dibenzofuranone and 23.4 g (0.1 M) of (2-ethoxy 2-phenyl)ethyl piperazine were introduced into a reactor, containing 200 ml of absolute ethanol.

After dissolution had taken place, 7.98 g (0.266 M) of polyoxymethylene were added and the mixture was refluxed for 2 hours. The mixture was then allowed to return to about 50° C., after which 4 g (0.133 M) of polyoxymethylene were further added. The mixture was again refluxed for 2 hours. At the end of the reaction, the ethanol was evaporated at reduced pressure.

The residue was dissolved in water and sodium-hydroxide was added to revert to a basic medium. The title product was extracted with methylene chloride and dried over sodium sulphate, the solvent was evaporated and the residue taken up in anhydrous acetone. By passing dry hydrogen chloride gas through the solution of title product was precipitated in the form of the dihydrochloride monohydrate.

After recrystallisation from ethanol, 32.5 g of product were obtained, having a melting point F=182.7° C. and the following elementary analysis:

| | C % | H % | N % |
| --- | --- | --- | --- |
| calculated | 61.71 | 7.29 | 5.33 |
| found | 62.45 | 7.23 | 5.41 |

EXAMPLE 2

1,2,3,4,4a,9b-hexahydro-4a-(1-[4-(2-ethoxy-2-phenyl)ethyl]piperazinyl)methyl-4-dibenzofuranol 21.73 g (0.05 M) of 1,2,3,4,4a,9b-hexahydro-4a-(1-[4-(2-ethoxy-2-phenyl)ethyl]piperazinyl)methyl-4-dibenzofuranone were dissolved in 100 ml of methanol, then 1.97 g (0.05 M) of sodium borohydride were added and the mixture was kept at ambient temperature, with stirring, for 2 hours. After methanol had been evaporated and water added, the product formed was extracted with ether and dried over sodium sulphate. The ether was evaporated and the residue dissolved in acetone. The title product was precipitated in the form of the hydrochloride by passing dry hydrogen chloride gas through the solution.

15 g of the title product were obtained in the form of the dihydrochloride monohydrate, having a melting point F=238.6° C. and the following elementary analysis:

| | C % | H % | N % |
| --- | --- | --- | --- |
| calculated | 61.48 | 7.64 | 5.31 |
| found | 61.40 | 7.49 | 5.18 |

EXAMPLE 3

1,2,3,4,4a,9b-hexahydro-4a-(1-[4-(2-ethoxy-2-phenyl)ethyl]piperazinyl)methyl-8-fluoro-4-dibenzofuranol, 2 HCl.

In a first step, 20.6 g (0.1 M) of 1,2,3,4,4a,9b-hexahydro-8-fluoro-4-dibenzofuranone were reacted with 23.4 g of (2-ethoxy-2-phenyl)ethyl piperazine following the method described in detail in Example 1. 41.3 g of 1,2,3,4,4a,9b-hexahydro-4a-(1-[4-(2-ethoxy-2-phenyl)ethyl]piperazinyl)methyl-8-fluoro-4-dibenzofuranone dihydrochloride were obtained. In the second step, 20 g (0.044 M) of this ketone obtained were reduced with 2 g (0.053 M) of sodium borohydride, using the same process as that described in Example 2.

21 g of the compound (the title product) were thus obtained in the form of the dihydrochloride, having a melting point F=244.4° C. and the following elementary analysis:

| | C % | H % | N % |
| --- | --- | --- | --- |
| calculated | 61.48 | 7.07 | 5.31 |
| found | 60.89 | 7.22 | 5.35 |

EXAMPLE 4

Various other compounds of the invention were prepared according to the same processes as described in the previous examples.

Table II shows further characteristics of these compounds.

TABLE II

| Compound No. | $R_2$ | $R_4$ | $\underset{Y}{\overset{X}{\diagdown C \diagup}}$ | $R_5$ | Ar | Melting point (salt) |
|---|---|---|---|---|---|---|
| 1 [Example 2] | H | H | CHOH | —$C_2H_5$ | phenyl | 238,6° C. (2HCl, $H_2O$) |
| 2 [Example 3] | F | H | CHOH | —$C_2H_5$ | phenyl | 244,4° C. (2HCl) |
| 3 | H | —$OCH_3$ | C=O | —$C_2H_5$ | phenyl | 207,6° C. (2HCl) |
| 4 | H | —$OCH_3$ | CHOH | —$C_2H_5$ | phenyl | 235,8° C. (2HCl) |
| 5 [Example 1] | H | H | C=O | —$C_2H_5$ | phenyl | 182,7° C. (2HCl, $H_2O$) |
| 6 | —$OCH_3$ | H | CHOH | —$C_2H_5$ | phenyl | 227,4° C. (2HCl) |
| 7 | H | H | CHOH | —$CH_3$ | pyridyl-$CH_3$ | 208° C. (3HCl) |
| 8 | H | H | CHOH | —$CH_3$ | phenyl | 254,1° C. (2HCl) |
| 9 | H | H | CHOH | H | phenyl | 243,1° C. (2HCl) |

The symbols $R_1$ and $R_3$ represent hydrogen in all above mentioned compounds of formula I.

We claim:

1. A compound of the formula:

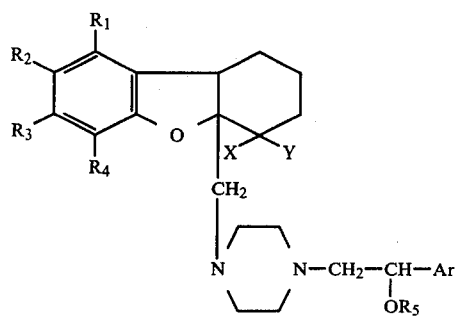

and pharmaceutically acceptable salts thereof, in which $R_1$, $R_2$, $R_3$ and $R_4$ are identical or different and represent hydrogen, halogen, lower alkyl or alkoxy or trifluoromethyl; $R_5$ represents hydrogen or lower alkyl, X represents hydrogen and Y represents hydroxy or X and Y together represent oxygen, and Ar represents an optionally substituted aromatic moiety, selected from the group consisting of phenyl or pyridyl optionally substituted with alkyl (1–4 C), alkoxy (1–4 C) or halogen.

2. Compound according to claim 1, characterised in that X and Y together represent oxygen.

3. Compound according to claim 1, characterised in that X represents hydrogen and Y represents hydroxy.

4. Compound according to claims 1, 2 or 3, characterised in that $R_1$ and $R_3$ represent hydrogen and $R_5$ represents hydrogen, methyl or ethyl.

5. Compound according to claims 1, 2 or 3, characterised in that Ar represents phenyl alkyl (1–4 C), substituted phenyl, 3-pyridyl or 4-methyl-3-pyridyl.

6. 1,2,3,4,4a,9b-hexahydro-4a-(1-(4-(2-alkoxy-2-phenyl)ethyl)piperazinyl)methyl-4-dibenzofuranol and pharmaceutically acceptable salts thereof.

7. Pharmaceutical composition, particularly useful for the treatment of dyspneas, characterised in that it contains, in combination with the usual pharmaceutical excipients, at least one compound according to one of the claims 1 to 6 as the active principle.

8. Pharmaceutical composition according to claim 7, having anti-bronchoconstrictor activity containing between 0,5 and 25 mg per kg body weight of the active principle.

* * * * *